(12) United States Patent
Mendelson

(10) Patent No.: US 6,801,799 B2
(45) Date of Patent: Oct. 5, 2004

(54) PULSE OXIMETER AND METHOD OF OPERATION

(75) Inventor: Yitzhak Mendelson, Worcester, MA (US)

(73) Assignee: Cybro Medical, Ltd., Haifa (IL)

( * ) Notice: Subject to any disclaimer, the term of this patent is extended or adjusted under 35 U.S.C. 154(b) by 0 days.

(21) Appl. No.: 10/360,666

(22) Filed: Feb. 6, 2003

(65) Prior Publication Data

US 2003/0144584 A1 Jul. 31, 2003

Related U.S. Application Data

(62) Division of application No. 09/939,391, filed on Aug. 24, 2001, now abandoned.

(30) Foreign Application Priority Data

Oct. 5, 2000 (IL) ................................ 138884

(51) Int. Cl.[7] ................................................. A61B 5/00
(52) U.S. Cl. ...................... 600/330; 600/322; 600/336
(58) Field of Search ................................. 600/310, 322, 600/323, 330, 336

(56) References Cited

U.S. PATENT DOCUMENTS

| | | |
|---|---|---|
| 3,638,640 A | 2/1972 | Shaw |
| 3,799,672 A | 3/1974 | Vurek ........................ 356/41 |
| 3,847,483 A | 11/1974 | Shaw ......................... 356/41 |
| 3,998,550 A | 12/1976 | Konishi et al. .............. 356/39 |
| 4,086,915 A | 5/1978 | Kofsky et al. |
| 4,167,331 A | 9/1979 | Nielsen ....................... 356/39 |
| 4,266,554 A | 5/1981 | Hamaguri |
| 4,357,105 A | 11/1982 | Loretz ........................ 356/40 |
| 4,407,290 A | 10/1983 | Wilber |
| 4,446,871 A | 5/1984 | Imura |
| 4,714,341 A | 12/1987 | Hamaguri et al. ........... 356/41 |
| 4,740,080 A | 4/1988 | Donohue et al. ........... 356/326 |
| 4,773,422 A | 9/1988 | Isaacson et al. |
| 4,796,636 A | 1/1989 | Branstetter et al. |
| 4,802,486 A | 2/1989 | Goodman et al. |
| 4,819,649 A | 4/1989 | Rogers et al. |
| 4,819,752 A | 4/1989 | Zelin |
| 4,854,699 A | 8/1989 | Edgar, Jr. .................... 356/41 |
| 4,859,057 A | 8/1989 | Taylor et al. ................. 356/41 |
| 4,867,557 A | 9/1989 | Takatani et al. .............. 356/41 |
| 4,892,101 A | 1/1990 | Cheung et al. |
| 4,928,692 A | 5/1990 | Goodman et al. |
| 4,934,372 A | 6/1990 | Corenman et al. |
| 4,960,126 A | 10/1990 | Conlon |
| 5,190,038 A | 3/1993 | Polson et al. |
| 5,224,478 A | 7/1993 | Sakai et al. |
| 5,348,004 A | 9/1994 | Hollub |
| 5,349,519 A | 9/1994 | Kaestle ................. 364/413.09 |

(List continued on next page.)

FOREIGN PATENT DOCUMENTS

| | | |
|---|---|---|
| WO | WO9403102 | 2/1994 |
| WO | WO0154573 | 8/2001 |
| WO | WO0184107 | 11/2001 |

OTHER PUBLICATIONS

"Reflecance Pulse Oximetry at the Forehead of Newborns: The Influenece of Varying Pressure on the Probe"; A. Carin M. Dassel, MD, et el.; Dept of Obstetrics and Gynecology, Univ. Hospital Groningen, Groningen; Journal of Clinical Monitoring 12: pp. 421–428, 1996.

(List continued on next page.)

Primary Examiner—Eric F. Winakur
(74) Attorney, Agent, or Firm—Howard & Howard

(57) ABSTRACT

A sensor for use in an optical measurement device and a method for non-invasive measurement of a blood parameter. The sensor includes sensor housing, a source of radiation coupled to the housing, and a detector assembly coupled to the housing. The source of radiation is adapted to emit radiation at predetermined frequencies. The detector assembly is adapted to detect reflected radiation at least one predetermined frequency and to generate respective signals. The signals are used to determine the parameter of the blood.

5 Claims, 6 Drawing Sheets

U.S. PATENT DOCUMENTS

| | | | |
|---|---|---|---|
| 5,355,880 A | | 10/1994 | Thomas et al. |
| 5,398,680 A | | 3/1995 | Polson et al. |
| 5,413,100 A | | 5/1995 | Barthelemy et al. |
| 5,421,329 A | | 6/1995 | Casciani et al. |
| 5,482,036 A | | 1/1996 | Diab et al. |
| 5,490,505 A | | 2/1996 | Diab et al. |
| 5,490,506 A | | 2/1996 | Takatani et al. |
| 5,494,032 A | * | 2/1996 | Robinson et al. ............ 600/323 |
| 5,517,988 A | | 5/1996 | Gerhard |
| 5,533,507 A | | 7/1996 | Potratz |
| 5,632,272 A | | 5/1997 | Diab et al. |
| 5,645,060 A | | 7/1997 | Yorkey |
| 5,685,299 A | | 11/1997 | Diab et al. |
| 5,758,644 A | | 6/1998 | Diab et al. |
| 5,769,785 A | | 6/1998 | Diab et al. .................. 600/364 |
| 5,782,237 A | | 7/1998 | Casciani et al. |
| 5,823,950 A | | 10/1998 | Diab et al. .................. 600/310 |
| 5,842,981 A | | 12/1998 | Larsen et al. ................ 600/323 |
| 5,853,364 A | | 12/1998 | Baker, Jr. et al. ............ 600/500 |
| 5,919,134 A | | 7/1999 | Diab .......................... 600/323 |
| 5,995,856 A | | 11/1999 | Mannheimer et al. ....... 600/322 |
| 6,011,986 A | | 1/2000 | Diab et al. .................. 600/323 |
| 6,031,603 A | | 2/2000 | Fine et al. .................... 356/41 |
| 6,036,642 A | | 3/2000 | Diab et al. .................. 600/364 |
| 6,067,462 A | | 5/2000 | Diab et al. .................. 600/310 |
| 6,081,735 A | | 6/2000 | Diab et al. .................. 600/310 |
| 6,083,172 A | | 7/2000 | Baker, Jr. et al. ............ 600/500 |

OTHER PUBLICATIONS

"Reflectance Pulse Oximetry—Principles and Obstetric Application in the Zurich System"; Voker Konig, Renate Huch, and Albert Huch; Perinatal Physiology Research Dept., Dept. of Obstetrics, Computing 14: pp. 403–412, 1998.

"Effect of location of the sensor on reflectance pulse oximetry"; A.C. M. Dassel, Research Fellow et al. British Journal of Obstetrics and Gynecology; Aug. 1997, vol. 104, pp. 910–916.

"Design and Evaluation of a New Reflectance Pulse Oximeter Sensor"; Y. Mendelson, PhD, et al.; Worcester Polytechnic Institute, Biomedical Engineering Program, Worcester, MA 01609; Association for the Advancement of Medical Instrumentation, vol. 22, No. 4, 1988; pp. 167–173.

"Skin Reflectance Pulse Oximetry: In Vivo Measurements from the Forearm and Calf"; Y. Mednelson, PhD and M.J. McGinn, MSc; Dept. of Biomedical Engineering, Worcester Polytechnic Institute, Worcester, MA 01609; Journal of Clinical Monitoring, vol. 7, No. 1, 1991; pp. 7–12.

"Experimental and Clinical Evaluation of a Noninvasive Reflectance Pulse Oximeter Sensor"; Setsuo Takatani, PhD, et al.; Dept. of Surgery, Baylor College of Medicine, One Baylor Plaza, Houston, TX 77030; Journal of Clinical Monitoring, vol. 8, No. 4, Oct. 1992; pp. 257–266.

"Wavelength Selection for Low–Saturation Pulse Oximetry"; Paul D. Mannheimer, et al.; IEEE Transactions on Biomedical Engineering, vol. 44, No. 3, Mar. 1997; pp. 148–158.

"Noninvasive Pulse Oximetry Utilizing Skin Reflectance Photoplethysmography"; Yitzhak Mendelson and Burt D. Ochs; IEEE Transactions on Biomedical Engineering, vol. 35, No. 10, Oct. 1988; pp. 798–805.

"Physio–optical considerations in the design of fetal pulse oximetry sensors"; P.D. Mannheimer, M.E. Fein and J.R. Casciani; European Journal of Obstetrics & Gynecology and Reproductive Biology 72 Suppl. 1 (1997) S9–S19.

"Fetal pulse oximetry: influence of tissue blood content and hemoglobin concentration in a new in–vitro model"; Thomas Edrich, Gerhard Rall, Reinhold Knitza; European Journal if Obstetrics & Gynecology and Reproductive Biology 72 Suppl. 1 (1997) S29–S34.

* cited by examiner

PULSE OXIMETER AND METHOD OF OPERATION

This application is a divisional application of U.S. patent application Ser. No. 09/939,391 filed Aug. 24, 2001, now abandoned.

BACKGROUND OF THE INVENTION

1. Field of the Invention

This invention is generally in the field of pulse oximetry, and relates to a sensor for use in a pulse oximeter, and a method for the pulse oximeter operation.

2. Background of the Invention

Oximetry is based on spectrophotometric measurements of changes in the color of blood, enabling the non-invasive determination of oxygen saturation in the patient's blood. Generally, oximetry is based on the fact that the optical property of blood in the visible (between 500 and 700 nm) and near-infrared (between 700 and 1000 nm) spectra depends strongly on the amount of oxygen in blood.

Referring to FIG. 1, there is illustrated a hemoglobin spectra measured by oximetry based techniques. Graphs G1 and G2 correspond, respectively, to reduced hemoglobin, or deoxyhemoglobin (Hb), and oxygenated hemoglobin, or oxyhemoglobin ($HbO_2$), spectra. As shown, deoxyhemoglobin (Hb) has a higher optical extinction (i.e., absorbs more light) in the red region of spectrum around 660 nm, as compared to that of oxyhemoglobin ($HbO_2$). On the other hand, in the near-infrared region of the spectrum around 940 nm, the optical absorption by deoxyhemoglobin (Hb) is lower than the optical absorption of oxyhemoglobin ($HbO_2$).

Prior art non-invasive optical sensors for measuring arterial oxyhemoglobin saturation ($SaO_2$) by a pulse oximeter (termed $SpO_2$) are typically comprised of a pair of small and inexpensive light emitting diodes (LEDs), and a single highly sensitive silicon photodetector. A red (R) LED centered on a peak emission wavelength around 660 nm and an infrared (IR) LED centered on a peak emission wavelength around 940 nm are used as light sources.

Pulse oximetry relies on the detection of a photoplethysmographic signal caused by variations in the quantity of arterial blood associated with periodic contraction and relaxation of a patient's heart. The magnitude of this signal depends on the amount of blood ejected from the heart into the peripheral vascular bed with each systolic cycle, the optical absorption of the blood, absorption by skin and tissue components, and the specific wavelengths that are used to illuminate the tissue. $SaO_2$ is determined by computing the relative magnitudes of the R and IR photoplethysmograms. Electronic circuits inside the pulse oximeter separate the R and IR photoplethysmograms into their respective pulsatile (AC) and non-pulsatile (DC) signal components. An algorithm inside the pulse oximeter performs a mathematical normalization by which the time-varying AC signal at each wavelength is divided by the corresponding time-invariant DC component which results mainly from the light absorbed and scattered by the bloodless tissue, residual arterial blood when the heart is in diastole, venous blood and skin pigmentation.

Since it is assumed that the AC portion results only from the arterial blood component, this scaling process provides a normalized R/IR ratio (i.e., the ratio of AC/DC values corresponding to R- and IR-spectrum wavelengths, respectively), which is highly dependent on $SaO_2$, but is largely independent of the volume of arterial blood entering the tissue during systole, skin pigmentation, skin thickness and vascular structure. Hence, the instrument does not need to be re-calibrated for measurements on different patients. Typical calibration of a pulse oximeter is illustrated in FIG. 2 by presenting the empirical relationship between $SaO_2$ and the normalized R/IR ratio, which is programmed by the pulse oximeters' manufacturers.

Pulse oximeters are of two kinds operating, respectively, in transmission and reflection modes. In transmission-mode pulse oximetry, an optical sensor for measuring $SaO_2$ is usually attached across a fingertip, foot or earlobe, such that the tissue is sandwiched between the light source and the photodetector.

In reflection-mode or backscatter type pulse oximetry, as shown in FIG. 3, the LEDs and photodetector are both mounted side-by-side next to each other on the same planar substrate. This arrangement allows for measuring $SaO_2$ from multiple convenient locations on the body (e.g. the head, torso, or upper limbs), where conventional transmission-mode measurements are not feasible. For this reason, non-invasive reflectance pulse oximetry has recently become an important new clinical technique with potential benefits in fetal and neonatal monitoring. Using reflectance oximetry to monitor $SaO_2$ in the fetus during labor, where the only accessible location is the fetal scalp or cheeks, or on the chest in infants with low peripheral perfusion, provides several more convenient locations for sensor attachment.

Reflection pulse oximetry, while being based on similar spectrophotometric principles as the transmission one, is more challenging to perform and has unique problems that can not always be solved by solutions suitable for solving the problems associated with the transmission-mode pulse oximetry. Generally, comparing transmission and reflection pulse oximetry, the problems associated with reflection pulse oximetry consist of the following:

In reflection pulse oximetry, the pulsatile AC signals are generally very small and, depending on sensor configuration and placement, have larger DC components as compared to those of transmission pulse oximetry. As illustrated in FIG. 4, in addition to the optical absorption and reflection due to blood, the DC signal of the R and IR photoplethysmograms in reflection pulse oximetry can be adversely affected by strong reflections from a bone. This problem becomes more apparent when applying measurements at such body locations as the forehead and the scalp, or when the sensor is mounted on the chest over the ribcage. Similarly, variations in contact pressure between the sensor and the skin can cause larger errors in reflection pulse oximetry (as compared to transmission pulse oximetry) since some of the blood near the superficial layers of the skin may be normally displaced away from the sensor housing towards deeper subcutaneous structures. Consequently, the highly reflective bloodless tissue compartment near the surface of the skin can cause large errors even at body locations where the bone is located too far away to influence the incident light generated by the sensor.

Another problem with currently available reflectance sensors is the potential for specular reflection caused by the superficial layers of the skin, when an air gap exists between the sensor and the skin, or by direct shunting of light between the LEDs and the photodetector through a thin layer of fluid which may be due to excessive sweating or from amniotic fluid present during delivery.

It is important to keep in mind the two fundamental assumptions underlying the conventional dual-wavelength pulse oximetry, which are as follows:

(1) the path of light rays with different illuminating wavelengths in tissue are substantially equal and, therefore, cancel each other; and (2) each light source illuminates the same pulsatile change in arterial blood volume.

Furthermore, the correlation between optical measurements and tissue absorptions in pulse oximetry are based on the fundamental assumption that light propagation is determined primarily by absorbable due to Lambent-Beer's law neglecting multiple scattering effects in biological tissues. In practice, however, the optical paths of different wavelengths in biological tissues is known to vary more in reflectance oximetry compared to transmission oximetry, since it strongly depends on the light scattering properties of the illuminated tissue and sensor mounting.

Several human validation studies, backed by animal investigations, have suggested that uncontrollable physiological and physical parameters can cause large variations in the calibration curve of reflectance pulse oximeters primarily at low oxygen saturation values below 70%. It was observed that the accuracy of pulse oximeters in clinical use might be adversely affected by a number of physiological parameters when measurements are made from sensors attached to the forehead, chest, or the buttock area. While the exact sources of these variations are not fully understood, it is generally believed that there are a few physiological and anatomical factors that may be the major source of these errors. It is also well known for example that changes in the ratio of blood to bloodless tissue volumes may occur through venous congestion, vasoconstriction/vasodilatation, or through mechanical pressure exerted by the sensor on the skin.

Additionally, the empirically derived calibration curve of a pulse oximeter can be altered by the effects of contact pressure exerted by the probe on the skin. This is associated with the following. The light paths in reflectance oximetry are not well defined (as compared to transmission oximetry), and thus may differ between the red and infrared wavelengths. Furthermore, the forehead and scalp areas consist of a relatively thin subcutaneous layer with the cranium bone underneath, while the tissue of other anatomical structures, such as the buttock and limbs, consists of a much thicker layer of skin and subcutaneous tissues without a nearby bony support that acts as a strong light reflector.

Several in vivo and in vitro studies have confirmed that uncontrollable physiological and physical parameters (e.g., different amounts of contact pressure applied by the sensor on the skin, variation in the ratio of bloodless tissue-to-blood content, or site-to-site variations) can often cause large errors in the oxygen saturation readings of a pulse oximeter, which are normally derived based on a single internally-programmed calibration curve. The relevant in vivo studies are disclosed in the following publications:

1. Dassel, et al., "Effect of location of the sensor on reflectance pulse oximetry", British Journal of Obstetrics and Gynecology, vol. 104, pp. 910–916, (1997);

2. Dassel, et al., "Reflectance pulse oximetry at the forehead of newborns: The influence of varying pressure on the probe", Journal of Clinical Monitoring, vol. 12, pp. 421–428, (1996).

The relevant in vitro studies are disclosed, for example in the following publication:

3. Edrich et al., "Fetal pulse oximetry: influence of tissue blood content and hemoglobin concentration in a new in-vitro model", European Journal of Obstetrics and Gynecology and Reproductive Biology, vol. 72, suppl. 1, pp. S29–S34, (1997).

Improved sensors for application in dual-wavelength reflectance pulse oximetry have been developed. As disclosed in the following publication: Mendelson, et al., "Noninvasive pulse oximetry utilizing skin reflectance photoplethysmography", IEEE Transactions on Biomedical Engineering, vol. 35, no. 10, pp. 798–805 (1988), the total amount of backscattered light that can be detected by a reflectance sensor is directly proportional to the number of photodetectors placed around the LEDs. Additional improvements in signal-to-noise ratio were achieved by increasing the active area of the photodetector and optimizing the separation distance between the light sources and photodetectors.

Another approach is based on the use of a sensor having six photodiodes arranged symmetrically around the LEDs that is disclosed in the following publications:

4. Mendelson, et al., "Design and evaluation of a new reflectance pulse oximeter sensor", Medical Instrumentation, vol. 22, no. 4, pp. 167–173 (1988); and 5. Mendelson, et al., "Skin reflectance pulse oximetry: in vivo measurements from the forearm and calf", Journal of Clinical Monitoring, vol. 7, pp. 7–12, (1991).

According to this approach, in order to maximize the fraction of backscattered light collected by the sensor, the currents from all six photodiodes are summed electronically by internal circuitry in the pulse oximeter. This configuration essentially creates a large area photodetector made of six discrete photodiodes connected in parallel to produce a single current that is proportional to the amount of light backscattered from the skin. Several studies showed that this sensor configuration could be used successfully to accurately measure $SaO_2$ from the forehead, forearm and the calf on humans. However, this sensor requires a means for heating the skin in order to increase local blood flow, which has practical limitations since it could cause skin burns.

Yet another prototype reflectance sensor is based on eight dual-wavelength LEDs and a single photodiode, and is disclosed in the following publication: Takatani et al., "Experimental and clinical evaluation of a noninvasive reflectance pulse oximeter sensor", Journal of Clinical Monitoring, vol. 8, pp. 257–266 (1992). Here, four R and four IR LEDs are spaced at 90-degree intervals around the substrate and at an equal radial distance from the photodiode.

A similar sensor configuration based on six photodetectors mounted in the center of the sensor around the LEDs is disclosed in the following publication: Konig, et al., "Reflectance pulse oximetry—principles and obstetric application in the Zurich system", Journal of Clinical Monitoring, vol. 14, pp. 403–412 (1998).

According to the techniques disclosed in all of the above publications, only LEDs of two wavelengths, R and IR, are used as light sources, and the computation of $SaO_2$ is based on reflection photoplethysmograms measured by a single photodetector, regardless of whether one or multiple photodiodes chips are used to construct the sensor. This is because of the fact that the individual signals from the photodetector elements are all summed together electronically inside the pulse oximeter. Furthermore, while a radially-symmetric photodetector array can help to maximize the detection of backscattered light from the skin and minimize differences from local tissue inhomogeneity, human and animal studies confirmed that this configuration can not completely eliminate errors caused by pressure differences and site-to-site variations.

The use of a nominal dual-wavelength pair of 735/890 nm was suggested as providing the best choice for optimizing accuracy, as well as sensitivity in dual-wavelength reflectance pulse oximetry, in U.S. Pat. Nos. 5,782,237 and 5,421,329. This approach minimizes the effects of tissue heterogeneity and enables to obtain a balance in path length changes arising from perturbations in tissue absorbance. This is disclosed in the following publications:

6. Mannheimer at al., "Physio-optical considerations in the design of fetal pulse oximetry sensors", European Journal of Obstetrics and Gynecology and Reproductive Biology, vol. 72, suppl. 1, pp. S9–S19, (1997); and 7. Mannheimer at al., "Wavelength selection for low-saturation pulse oximetry", IEEE Transactions on Biomedical Engineering, vol. 44, no. 3, pp. 48–158 (1997)].

However, replacing the conventional R wavelength at 660 nm, which coincides with the region of the spectrum where the difference between the extinction coefficient of Hb and $HbO_2$ is maximal, with a wavelength emitting at 735 nm, not only lowers considerably the overall sensitivity of a pulse oximeter, but does not completely eliminate errors due to sensor placement and varying contact pressures.

Pulse oximeter probes of a type comprising three or more LEDs for filtering noise and monitoring other functions, such as carboxyhemoglobin or various indicator dyes injected into the blood stream, have been developed and are disclosed, for example, in WO 00/32099 and U.S. Pat. No. 5,842,981. The techniques disclosed in these publications are aimed at providing an improved method for direct digital signal formation from input signals produced by the sensor and for filtering noise.

None of the above prior art techniques provides a solution to overcome the most essential limitation in reflectance pulse oximetry, which requires the automatic correction of the internal calibration curve from which accurate and reproducible oxygen saturation values are derived, despite variations in contact pressure or site-to-site tissue heterogeneity.

In practice, most sensors used in reflection pulse oximetry rely on closely spaced LED wavelengths in order to minimize the differences in the optical path lengths of the different wavelengths. Nevertheless, within the wavelength range required for oximetry, even closely spaced LEDs with closely spaced wavelengths mounted on the same substrate can lead to large random error in the final determination of $SaO_2$.

SUMMARY OF THE INVENTION AND ADVANTAGES

The object of the invention is to provide a novel sensor design and method that functions to correct the calibration relationship of a reflectance pulse oximeter, and reduce measurement inaccuracies in general. Another object of the invention is to provide a novel sensor and method that functions to correct the calibration relationship of a reflectance pulse oximeter, and reduce measurement inaccuracies in the lower range of oxygen saturation values (typically below 70%), which is the predominant range in neonatal and fetal applications.

Yet another object of the present invention is to provide automatic correction of the internal calibration curve from which oxygen saturation is derived inside the oximeter in situations where variations in contact pressure or site-to-site tissue heterogeneity may cause large measurement inaccuracies.

Another object of the invention is to eliminate or reduce the effect of variations in the calibration of a reflectance pulse oximeter between subjects, since perturbations caused by contact pressure remain one of the major sources of errors in reflectance pulse oximetry. In fetal pulse oximetry, there are additional factors, which must be properly compensated for in order to produce an accurate and reliable measurement of oxygen saturation. For example, the fetal head is usually the presenting part, and is a rather easily accessible location for application of reflectance pulse oximetry. However, uterine contractions can cause large and unpredictable variations in the pressure exerted on the head and by the sensor on the skin, which can lead to large errors in the measurement of oxygen saturation by a dual-wavelength reflectance pulse oximeter. Another object of the invention is to provide accurate measurement of oxygen saturation in the fetus during delivery.

The basis for the errors in the oxygen saturation readings of a dual-wavelength pulse oximeter is the fact that, in practical situations, the reflectance sensor applications affect the distribution of blood in the superficial layers of the skin. This is different from an ideal situation, when a reflectance sensor measures light backscattered from a homogenous mixture of blood and bloodless tissue components. Therefore, the R and IR DC signals practically measured by photodetectors contain a relatively larger proportion of light absorbed by and reflected from the bloodless tissue compartments. In these uncontrollable practical situations, the changes caused are normally not compensated for automatically by calculating the normalized R/IR ratio since the AC portions of each photoplethysmogram, and the corresponding DC components, are affected differently by pressure or site-to-site variations. Furthermore, these changes depend not only on wavelength, but depend also on the sensor geometry, and thus cannot be eliminated completely by computing the normalized R/IR ratio, as is typically the case in dual-wavelength pulse oximeters.

The inventor has found that the net result of this nonlinear effect is to cause large variations in the slope of the calibration curves. Consequently, if these variations are not compensated automatically, they will cause large errors in the final computation of $SpO_2$, particularly at low oxygen saturation levels normally found in fetal applications.

Another object of the present invention is to compensate for these variations and to provide accurate measurement of oxygen saturation. The invention consists of, in addition to two measurement sessions typically carried out in pulse oximetry based on measurements with two wavelengths centered around the peak emission values of 660 nm (red spectrum) and 940 nm±20 nm (IR spectrum), one additional measurement session is carried out with an additional wavelength. At least one additional wavelength is preferably chosen to be substantially in the IR region of the electromagnetic spectrum, i.e., in the NIR-IR spectrum (having the peak emission value above 700 nm). In a preferred embodiment the use of at least three wavelengths enables the calculation of an at least one additional ratio formed by the combination of the two IR wavelengths, which is mostly dependent on changes in contact pressure or site-to-site variations. In a preferred embodiment, slight dependence of the ratio on variations in arterial oxygen saturation that may occur, is easily minimized or eliminated completely, by the proper selection and matching of the peak emission wavelengths and spectral characteristics of the at least two IR-light sources.

Preferably, the selection of the IR wavelengths is based on certain criteria. The IR wavelengths are selected to coincide with the region of the optical absorption curve where $HbO_2$ absorbs slightly more light than Hb. The IR wavelengths are in the spectral regions where the extinction coefficients of both Hb and $HbO_2$ are nearly equal and remain relatively constant as a function of wavelength, respectively.

In a preferred embodiment, tracking changes in the ratio formed by the two IR wavelengths, in real-time, permits automatic correction of errors in the normalized ratio obtained from the R-wavelength and each of the IR-wavelengths. The term "ratio" signifies the ratio of two values of AC/DC corresponding to two different wavelengths. This is similar to adding another equation to solve a problem with at least three unknowns (i.e., the relative concentrations of $HbO_2$ and Hb, which are used to calculate $SaO_2$, and the unknown variable fraction of blood-to-tissue volumes that effects the accurate determination of $SaO_2$), which otherwise must rely on only two equations in the case of only two wavelengths used in conventional dual-wavelength pulse oximetry. In a preferred embodiment, a third wavelength provides the added ability to compute $SaO_2$ based on the ratio formed from the R-wavelength and either of the IR-wavelengths. In a preferred embodiment, changes in these ratios are tracked and compared in real-time to determine which ratio produces a more stable or less noisy signal. That ratio is used predominantly for calculating $SaO_2$.

The present invention utilizes collection of light reflected from the measurement location at different detection locations arranged along a closed path around light emitting elements, which can be LEDs or laser sources. Preferably, these detection locations are arranged in two concentric rings, the so-called "near" and "far" rings, around the light emitting elements. This arrangement enables optimal positioning of the detectors for high quality measurements, and enables discrimination between photodetectors receiving "good" information (i.e., AC and DC values which would result in accurate calculations of $SpO_2$) and "bad" information (i.e., AC and DC values which would result in inaccurate calculations of $SpO_2$).

There is thus provided according to one aspect of the present invention, a sensor for use in an optical measurement device for non-invasive measurements of blood parameters, the sensor comprising:

(1) a light source for illuminating a measurement location with incident light of at least three wavelengths, the first wavelength lying in a red (R) spectrum, and the at least second and third wavelengths lying substantially in the infrared (IR) spectrum; and (2) a detector assembly for detecting light returned from the illuminated location, the detector assembly being arranged so as to define a plurality of detection locations along at least one closed path around the light source.

The term "closed path" used herein signifies a closed curve, like a ring, ellipse, or polygon, and the like.

The detector assembly is comprised of at least one array of discrete detectors (e.g., photodiodes) accommodated along at least one closed path, or at least one continuous photodetector defining the closed path.

The term "substantially IR spectrum" used herein signifies a spectrum range including near infrared and infrared regions.

According to another aspect of the present invention, there is provided a pulse oximeter utilizing a sensor constructed as defined above, and a control unit for operating the sensor and analyzing data generated thereby.

According to yet another aspect of the present invention, there is provided a method for non-invasive determination of a blood parameter, the method comprising the steps of:

illuminating a measurement location with at least three different wavelengths $\lambda 1$, $\lambda 2$ and $\lambda 3$, the first wavelength $\lambda 1$ lying in a red (R) spectrum, and the at least second and at least third wavelengths $\lambda 2$ and $\lambda 3$ lying substantially in the infrared (IR) spectrum;

detecting light returned from the measurement location at different detection locations and generating data indicative of the detected light, wherein said different detection locations are arranged so as to define at least one closed path around the measurement location; and analyzing the generated data and determining the blood parameter.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE PREFERRED EMBODIMENTS

Figure 1:
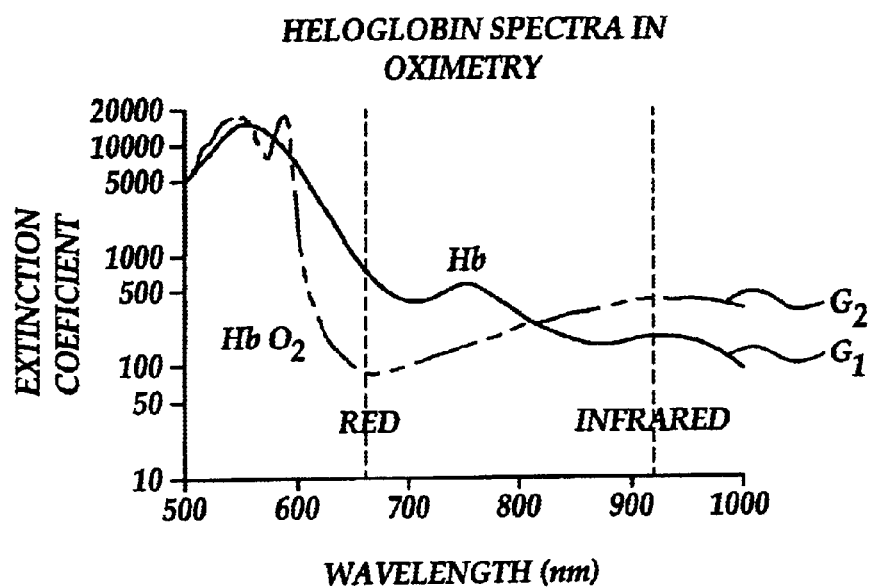
FIG. 1 illustrates hemoglobin spectra as measured by oximetry based techniques.
Figure 2:
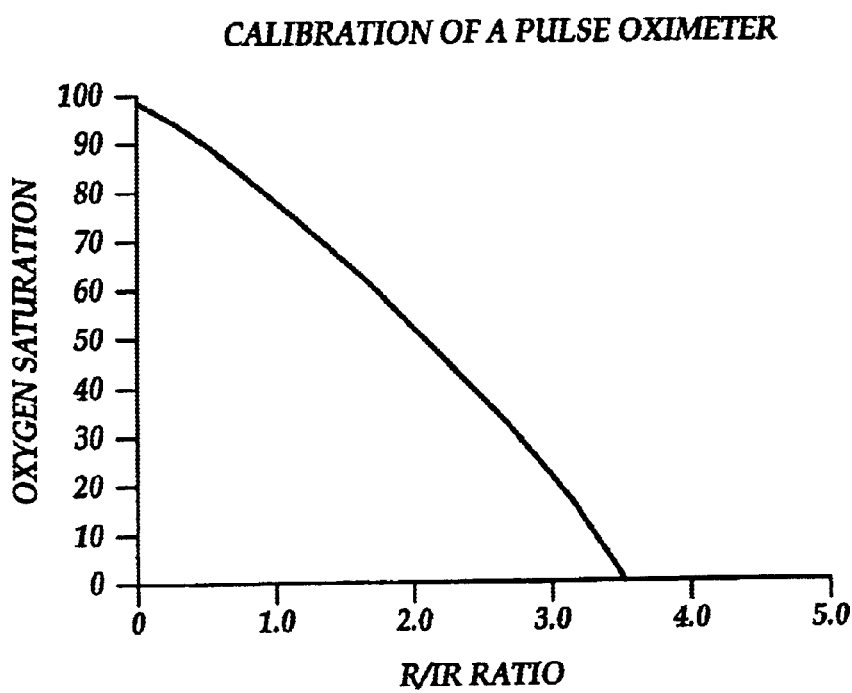
FIG. 2 illustrates a calibration curve used in pulse oximetry as typically programmed by the pulse oximeters manufacturers.

Referring to the Figures, wherein like numerals indicate like or corresponding parts throughout the several views, FIGS. 1 and 2 illustrate typical hemoglobin spectra and calibrations curve utilized in the pulse oximetry measurements.

Figure 3:
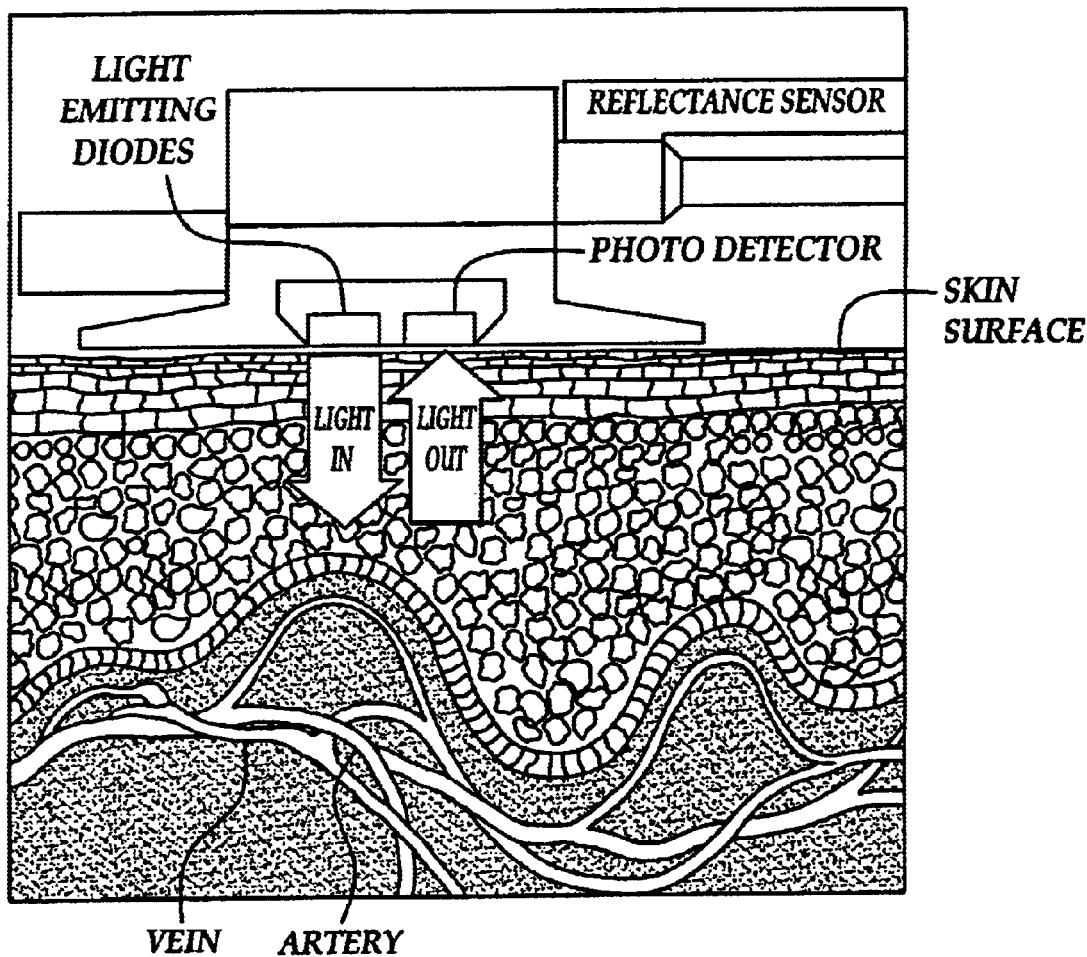
FIG. 3 illustrates the relative disposition of light source and detector in reflection-mode or backscatter type pulse oximetry.

The present invention provides a sensor for use in a reflection-mode or backscatter type pulse oximeter. The relative disposition of light source and detector in the reflection-mode pulse oximeter are illustrated in FIG. 3.

Figure 4:
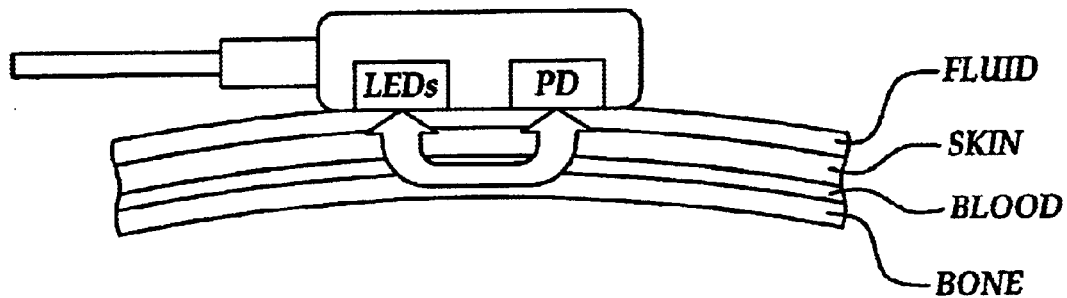
FIG. 4 illustrates light propagation in reflection pulse oximetry.

FIG. 4 shows light propagation in the reflection-mode pulse oximeter where, in addition to the optical absorption and reflection due to blood, the DC signal of the R and IR photoplethysmograms can be adversely affected by strong reflections from the bone.

Figure 5A:
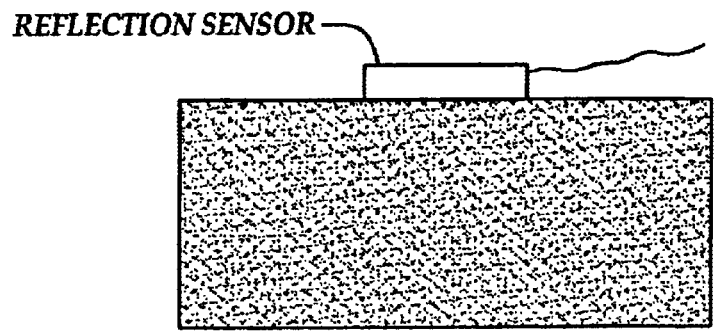
FIGS. 5A and 5B illustrate a pulse oximeter reflectance sensor operating under ideal and practical conditions, respectively.
Figure 5B:
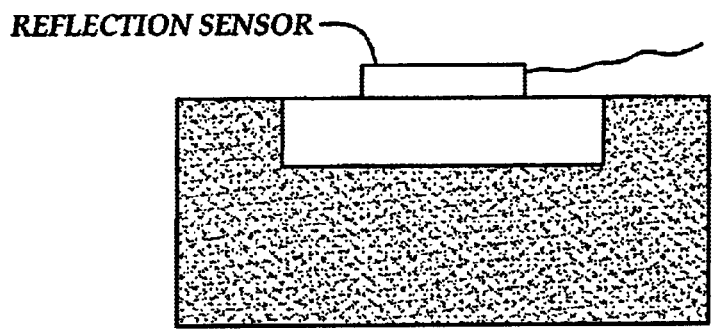

FIGS. 5A and 5B illustrate a pulse oximeter reflectance sensor operating under, respectively, ideal and practical conditions. Referring now to FIG. 5A, it is shown that, under ideal conditions, reflectance sensor measures light backscattered from a homogenous mixture of blood and bloodless tissue components. Accordingly, the normalized R/IR ratio in dual-wavelength reflection type pulse oximeters, which relies on proportional changes in the AC and DC components in the photoplethysmograms, only reflect changes in arterial oxygen saturation.

Figure 6:
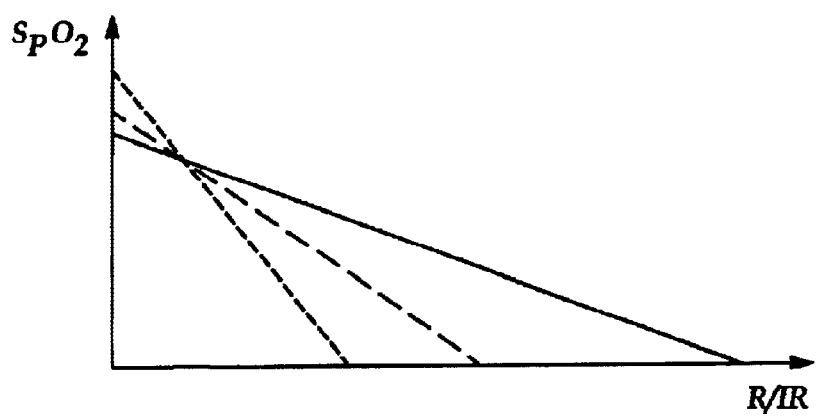
FIG. 6 illustrates variations of the slopes of calibration curves in reflectance pulse oximetry measurements.

Referring now to FIG. 5B, in practical situations, the sensor applications affect the distribution of blood in the superficial layers of the skin. Accordingly, the R and IR DC signals measured by photodetectors contain a relatively larger proportion of light absorbed by and reflected from the bloodless tissue compartments. As such, the changes in DC signals depend not only on wavelength but also sensor geometry and thus cannot be eliminated completely by computing the normalized R/IR ratio, as is typically the case in dual-wavelength pulse oximeters. The result is large variations in the slope of the calibration curves, as illustrated in FIG. 6. Referring now to FIG. 6, graphs C1, C2 and C3 show three calibration curves, presenting the variation of the slope for oxygen saturation values between 50% and 100%.

Figure 7:
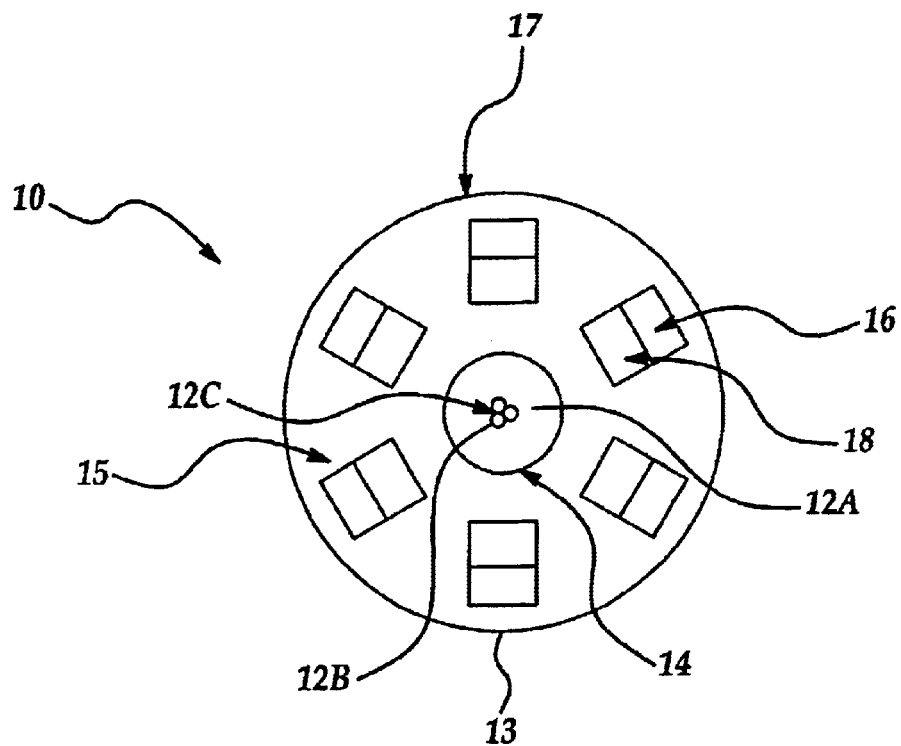
FIG. 7 illustrates an optical sensor according to the invention.

Referring to FIG. 7, there is illustrated an optical sensor 10 designed according to the invention aimed at minimizing some of the measurement inaccuracies in a reflectance pulse oximeter. The sensor 10 comprises such main constructional parts as a light source 12 composed of three closely spaced light emitting elements (e.g., LEDs or laser sources) 12a, 12b and 12c generating light of three different wavelengths, respectively; an array of discrete detectors (e.g., photodiodes), a "far" detector 16 and a "near" detector 18, arranged in two concentric ring-like arrangements (constituting closed paths) surrounding the light emitting elements; and a light shield 14. In the present example, six photodiodes form each ring. All these elements are accommodated in a sensor housing 17. The light shield 14 is positioned between the photodiodes and the light emitting elements, and prevents direct optical coupling between them, thereby maximizing the fraction of backscattered light passing through the arterially perfused vascular tissue in the detected light.

It should be noted that more than three wavelengths can be utilized in the sensor. The actual numbers of wavelengths used as a light source and the number of photodetectors in each ring are not limited and depend only on the electronic circuitry inside the oximeter. The array of discrete photodiodes can be replaced by one or more continuous photodetector rings.

In addition to the R and IR light emitting elements 12a and 12b as used in the conventional pulse oximeter sensors, the sensor 10 incorporates the third, reference, light emitting element 12c, which emits light in the NIR-IR spectrum. Wavelength $\lambda 1$ and $\lambda 2$ of the R and IR light emitting elements 12a and 12b are centered, respectively, around the peak emission values of 660 nm and 940 nm, and wavelength $\lambda 3$ of the third light emitting element 12c has the peak emission value above 700 nm (typically ranging between 800 nm and 900 nm). In the description below, the light emitting elements 12b and 12c are referred to as two IR light emitting elements, and wavelengths $\lambda 2$ and $\lambda 3$ are referred to as two IR wavelengths.

During the operation of the sensor 10, different light emitting elements are selectively operated for illuminating a measurement location (not shown) with different wavelengths. Each of the photodetectors detects reflected light of different wavelengths and generates data indicative of the intensity I of the detected light of different wavelengths.

It should be noted that the sensor can be of a compact design utilizing an integrated circuit manufactured by CMOS technology. This technique is disclosed in a co-pending application assigned to the assignee of the present application. According to this technique, the sensor comprises a package including the light source, a block of two tubular optical waveguides of different diameters concentrically dislocated one inside the other and surrounding the light source, and an integrated circuit plate comprising two ring-like areas of photodiodes positioned concentrically one inside the other. The integrated circuit is also provided with a plurality of printed contact areas and electric conductors intended for mounting the light source thereon, controlling the light source, and transmitting electric signals produced by the photodiodes areas for further processing.

Figure 8:
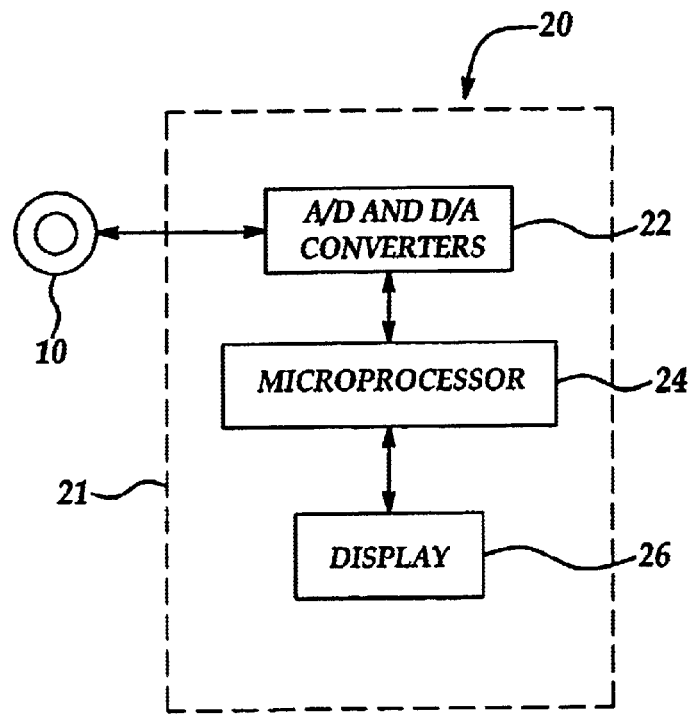
FIG. 8 is a block diagram of the main components of a pulse oximeter utilizing the sensor of FIG. 7.

FIG. 8 illustrates a block diagram of a pulse oximeter 20 utilizing the above-described sensor 10. The pulse oximeter typically includes a control unit 21, which is composed of an electronic block 22 including A/D and D/A converters connectable to the sensor 10, a microprocessor 24 for analyzing measured data, and a display 26 for presenting measurement results. The measured data (i.e., electrical output of the sensor 10 indicative of the detected light) is directly processed in the block 22, and the converted signal is further processed by the microprocessor 24. The microprocessor 24 is operated by a suitable software model for analyzing the measured data and utilizing reference data (i.e., calibration curve stored in a memory) to compute the oxygen saturation value, which is then presented on the display 26. The analysis of the measured data utilizes the determination of AC- and DC-components in the detected light for each wavelength, $\lambda 1$, $\lambda 2$, and $\lambda 3$, respectively, i.e., $I_1^{(AC)}$, $I_1^{(DC)}$, $I_2^{(AC)}$, $I_2^{(DC)}$, $I_3^{(AC)}$, and $I_3^{(DC)}$, and the calculation of AC/DC ratio for each wavelength, namely, $W_1=I_1^{(AC)}/I_1^{(DC)}$, $W_2=I_2^{(AC)}/I_2^{(DC)}$, and $W_3=I_3^{(AC)}/I_3^{(DC)}$, as will be described more specifically further below with reference to FIGS. 9 and 10A–10C.

The pulse oximeter 20 with the sensor arrangement shown in FIG. 7 provides the following three possible ratio values: $W_1/W_2$, $W_1/W_3$ and $W_2/W_3$. It should be noted that $W_1/W_2$ and $W_1/W_3$ are the ratios that typically have the highest sensitivity to oxygen saturation. This is due to the fact that $\lambda 1$ is chosen in the red region of the electromagnetic spectrum, where the changes in the absorption between Hb and $HbO_2$ are the largest, as described above with reference to FIG. 1. Therefore, in principle, the absorption ratios formed by either wavelength pair $\lambda 1$ and $\lambda 2$ or wavelength pair $\lambda 1$ and $\lambda 3$ can be used to compute the value of $SaO_2$.

The inventor conducted extensive human and animal studies, and confirmed that either of the two ratios $W_1/W_2$ and $W_1/W_3$ can be affected not only by changes in arterial oxygen saturation, but also by sensor placement and by the amount of pressure applied by the sensor on the skin. Any calculation of $SaO_2$ based on either of the two ratios $W_1/W_2$ and $W_1/W_3$ alone (as normally done in commercially available dual-wavelength pulse oximeters) could result in significant errors. Furthermore, since at least two wavelengths are necessary for the calculation of arterial oxygen saturation, it is not feasible to self-correct the calibration curve for variations due to contact pressure or site-to-site variations utilizing the same two wavelengths used already to compute $SaO_2$.

The inventor has found that the third ratio $W_2/W_3$ formed by the combination of the two IR wavelengths is mostly dependent on changes in contact pressure or site-to-site variations. Furthermore, this ratio can depend, but to a much lesser degree, on variations in arterial oxygen saturation.

The dependency on arterial oxygen saturation, however, is easily minimized or eliminated completely, for example by selection and matching of the peak emission wavelengths and spectral characteristics of the two IR light emitting elements 12b and 12c.

Generally, the two IR wavelengths $\lambda 2$ and $\lambda 3$ are selected to coincide with the region of the optical absorption curve where $HbO_2$ absorbs slightly more light than Hb, but in the spectral region, respectively, where the extinction coefficients of both Hb and $HbO_2$ are nearly equal and remain relatively constant as a function of wavelength. For example, at 940 nm and 880 nm, the optical extinction coefficients of Hb and $HbO_2$ are approximately equal to 0.29 and 0.21, respectively. Therefore, ideally, the ratio of W2/W3 should be close to 1, except for situations when the AC/DC signals measured from $\lambda 2$ and $\lambda 3$ are affected unequally causing the ratio W2/W3 to deviate from 1.

Fortunately, variations in the ratio W2/W3 mimic changes in the ratios $W_1/W_2$ and $W_1/W_3$ since these ratios are all affected by similar variations in sensor positioning or other uncontrollable factors that normally can cause large errors in the calibration curve from which oxygen saturation is typically derived. Thus, by tracking in real-time changes in the ratio formed by wavelengths $\lambda 2$ and $\lambda 3$, it is possible to automatically correct for errors in the normalized ratios obtained from wavelengths $\lambda 1$ and $\lambda 2$, or from $\lambda 1$ and $\lambda 3$.

The use of an additional third wavelength in the sensor serves another important function (not available in conventional dual-wavelength pulse oximeters), which is associated with the following. Reflectance pulse oximeters have to be capable of detecting and relying on the processing of relatively low quality photoplethysmographic signals. Accordingly, electronic or optical noise can cause large inaccuracies in the final computation of $SaO_2$. Although the amount of electronic or optical noise pickup from the sensor can be minimized to some extent, it is impossible to render the signals measured by the pulse oximeter completely noise free. Therefore, pulse oximeters rely on the assumption that any noise picked up during the measurement would be cancelled by calculating the ratio between the R- and IR-light intensities measured by the photodetector. Practically, however, the amount of noise that is superimposed on the R- and IR-photoplethysmograms cannot be cancelled completely and, thus, can lead to significant errors in the final computation of $SaO_2$ which, in dual-wavelength pulse oximeters, is based only on the ratio between two wavelengths.

By utilizing a third wavelength, the invention has the added ability to compute $SaO_2$ based on the ratio formed from either $W_1/W_2$ or $W_1/W_3$. An algorithm utilized in the pulse oximeter according to the invention has the ability to track and compare in real-time changes between $W_1/W_2$ and $W_1/W_3$ to determine which ratio produces a more stable or less noisy signal and selectively choose the best ratio for calculating $SaO_2$.

Figure 9:
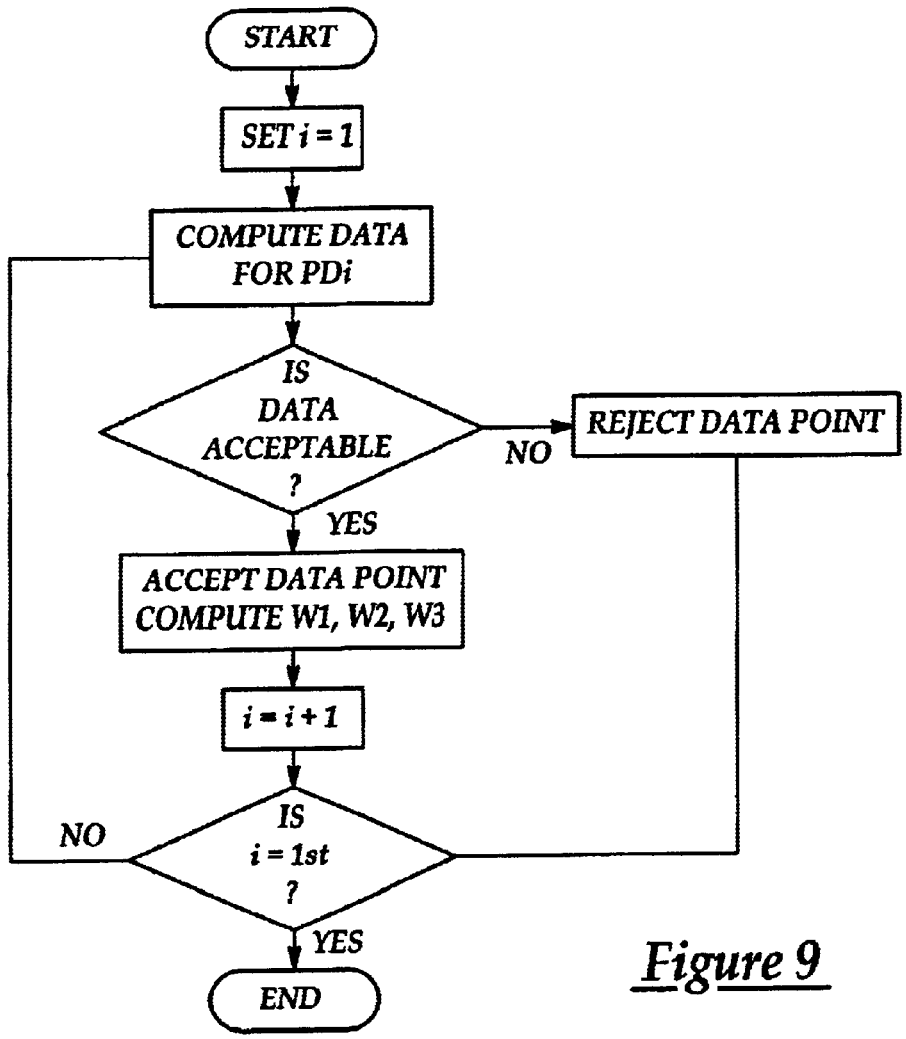
FIG. 9 is a flow chart of a selection process used in the signal processing technique according to the invention.

The method according to the invention utilizes the so-called "selection process" as part of the signal processing technique based on the measured data obtained with the multiple photodetectors. The main steps of the selection process are shown in FIG. 9 in a self-explanatory manner. Here, the symbol i corresponds to a single photodetector element in the array of multiple discrete photodetector elements, the term "1st" signifies the last photodetector element in the array, and the term "DATA" signify three ratios (AC/DC) computed separately for each of the three wavelengths, namely, $W_1$, $W_2$ and $W_3$.

The selection process is associated with the following: Practically, each time one of the light emitting elements is in its operative position (i.e., switched on), all of the photodetectors in the sensor receiving backscattered light from the skin. However, the intensity of the backscattered light measured by each photodetector may be different from that measured by the other photodetectors, depending on the anatomical structures underneath the sensor and its orientation relative to these structures.

Thus, the selection process is used to discriminate between photodetectors receiving "good" signals (i.e., "good" signal meaning that the calculation of $SpO_2$ from the pulsating portion of the electro-optic signal (AC) and the constant portion (DC) would result in accurate value) and "bad" signals (i.e., having AC and DC values which would result in inaccurate calculations of $SpO_2$). Accordingly, each data point (i.e., ratio $W_{1i}$, $W_{2i}$ or $W_{3i}$ detected at the corresponding $i^{th}$ detector) is either accepted, if it meets a certain criteria based for example on a certain ratio of AC to DC values (e.g., such that the intensity of AC signal is about 0.05–2.0% of the intensity of DC signal), or rejected. All of the accepted data points (data from accepted detection locations) are then used to calculate the ratios $W_1/W_2$, $W_1/W_3$ and $W_2/W_3$, and to calculate the $SpO_2$ value, in conjunction with the signal processing technique, as will be described further below with reference to FIGS. 10A–10C.

Besides the use of the third IR-wavelength to compensate for changes in the internal calibration curve of the pulse oximeter, the pulse oximeter utilizing the sensor according to the invention provides a unique new method to compensate for errors due to sensor positioning and pressure variability. This method is based on multiple photodetector elements, instead of the conventional approach that relies on a single photodetector.

While optical sensors with multiple photodetectors for application in reflectance pulse oximetry have been described before, their main limitation relates to the way the information derived from these photodetectors is processed. Although the primary purpose of utilizing multiple photodetectors is to collect a larger portion of the backscattered light from the skin, practically, summing the individual intensities of each photodetector and using the resulting value to compute $SaO_2$ can introduce large errors into the calculations. These errors can be caused, for example, by situations where the sensor is placed over inhomogeneous tissue structures such as when the sensor is mounted on the chest. The case may be such that, when using a continuous photodetector ring to collect the backscattered light, a portion of the photodetector ring lies over a rib, which acts as a strongly reflecting structure that contributes to a strong DC component, and the remaining part of the photodetector is positioned over the intercostals space, where the DC signal is much smaller. In this case, the final calculation of $SaO_2$ would be inaccurate, if the current produced by this photodetector is used indiscriminately to compute the DC value before the final computation of $SaO_2$ is performed. Therefore, in addition to automatically correcting errors in the calibration curve as outlined above using three different LEDs (one R and two different IR wavelengths), the sensor 10 has the optional ability to track automatically and compare changes in the R/IR ratios obtained from each of the discrete photodiodes individually. For example, if some of either the near or the far photodetectors in the two concentrically arranged arrays detect larger than normal DC signals during the operation of one of the photodiodes compared to the other photodiodes in the sensor, it could be indicative of one of the following situations: the sensor is positioned unevenly, the sensor is partially covering a bony structure, or uneven pressure is exerted by the sensor on the skin causing partial skin "blanching" and therefore the blood-to-bloodless tissue ratio might be too high to allow accurate determination of SaO$_2$. If such a situation is detected, the oximeter has the ability to selectively disregard the readings obtained from the corresponding photodetectors. Otherwise, if the DC and AC signals measured from each photodetector in the array are similar in magnitude, which is an indication that the sensor is positioned over a homogeneous area on the skin, the final computation of SaO$_2$ can be based on equal contributions from every photodetector in the array.

Figure 10A:
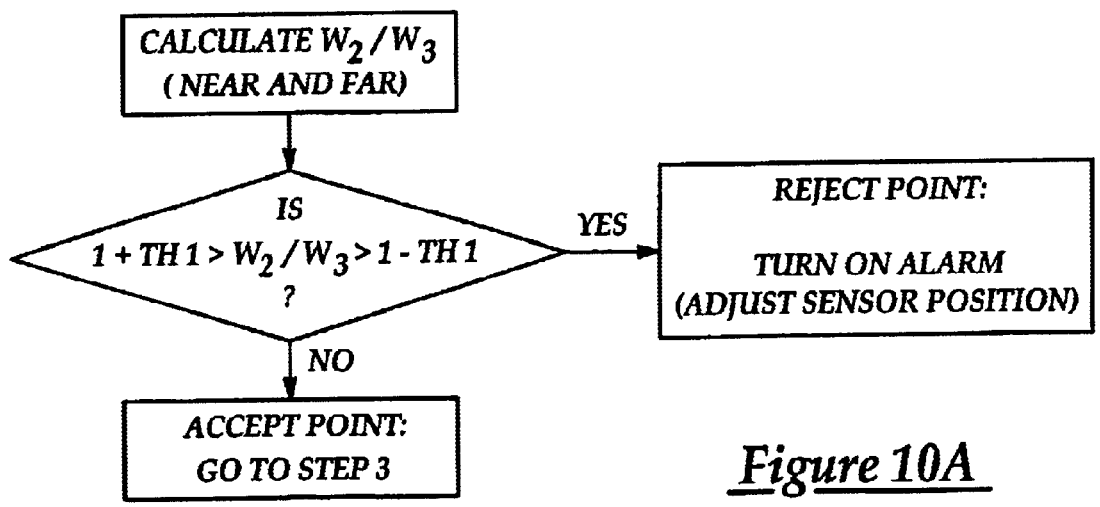
FIGS. 10A to 10C are flow charts of three main steps, respectively, of the signal processing method according to the invention.
Figure 10B:
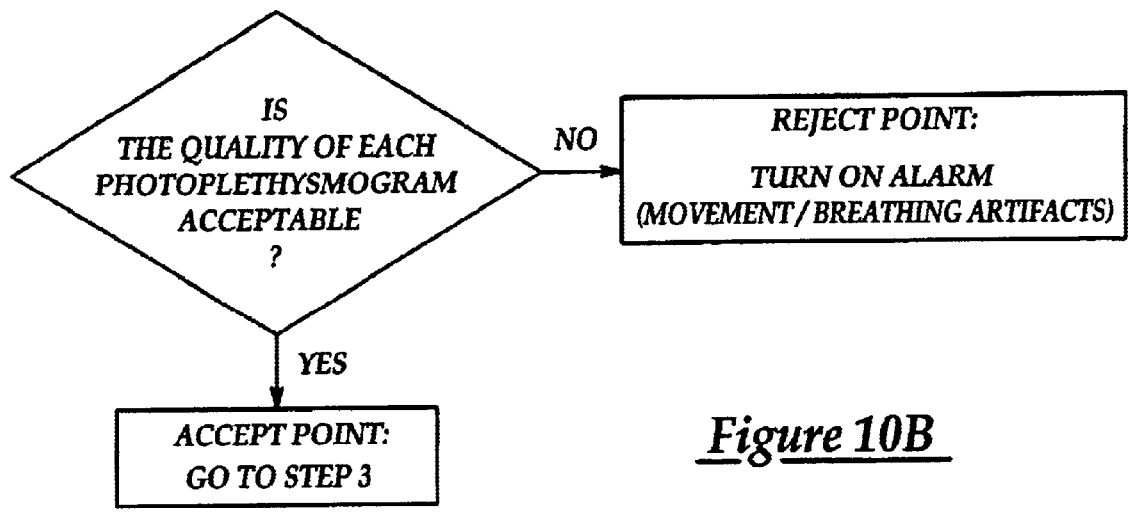
Figure 10C:
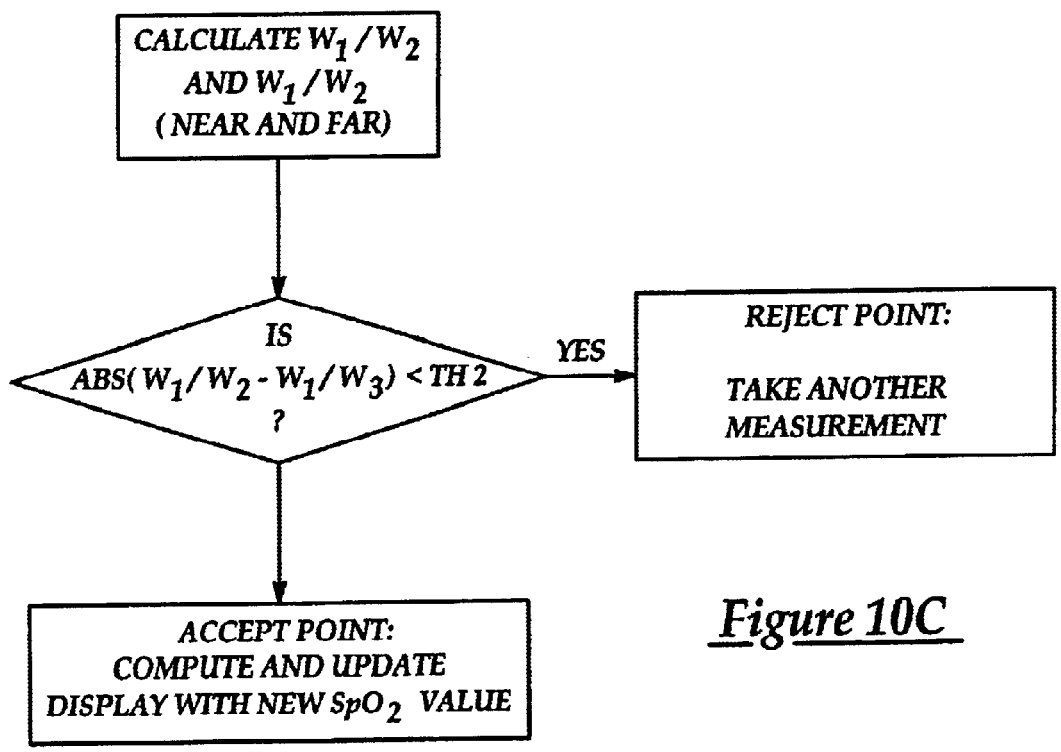

Turning now to FIGS. 10A, 10B and 10C, there are illustrated three main steps of the signal processing technique utilized in the present invention Here, TH$_1$ and TH$_2$ are two different threshold values (determined experimentally) related respectively to $W_2/W_3$ and $(W_1/W_2-W_1/W_3)$.

During step 1 (FIG. 10A), measured data generated by the "near" and "far" photodetectors indicative of the detected (backscattered) light of wavelength $\lambda 2$ and $\lambda 3$ is analyzed to calculate the two ratios $W_2/W_3$ (far and near). If one of the calculated ratios (far or near) is not in the range of $1\pm TH_1$ (TH$_1$ is for example 0.1), then this data point is rejected from the SpO$_2$ calculation, but if both of them are not in the mentioned range, a corresponding alarm is generated indicative of that the sensor position should be adjusted. Only if there are calculated ratios which are in the range of $1\pm TH1$, they are accepted and the process (data analysis) proceeds by performing step 2.

Step 2 (FIG. 10B) consists of determining whether the quality of each photoplethysmogram is acceptable or not. The quality determination is based on the relative magnitude of each AC component compared to its corresponding DC component. If the quality is not acceptable (e.g., the signal shape detected by any detector varies within a time frame of the measurement session, which may for example be 3.5 sec), the data point is rejected and a corresponding alarm signal is generated. If the AC/DC ratio of $W_1$, $W_2$ and $W_3$ are within an acceptable range, the respective data point is accepted, and the process proceeds through performing step 3.

In step 3 (FIG. 10C), the measured data is analyzed to calculate ratios $W_1/W_2$ and $W_1/W_3$ from data generated by far and near photodetectors, and to calculate the differences $(W_1/W_2-W_1/W_3)$.

In a perfect situation, $W_1/W_2$ (far) is very close to $W_1/W_3$ (far), and $W_1/W_2$ (near) is very close to $W_1/W_3$ (near). In a practical situation, this condition is not precisely satisfied, but all the ratios are close to each other if the measurement situation is "good".

Then, the calculated differences are analyzed to determine the values (corresponding to far and near photodetectors) that are accepted and to use them in the SpO$_2$ calculation. For each detector that satisfied the condition ABS($W_1/W_2-W_1/W_3$)<TH$_2$), where ABS signifies the absolute value, its respective data point is accepted and used to calculate the oxygen saturation value that will be displayed. If the condition is not satisfied, the data point is rejected. If all data points are rejected, another measurement session is carried out.

It should be noted that, although the steps 1–3 above are exemplified with respect to signal detection by both near and far photodetectors, each of these steps can be implemented by utilizing only one array of detection locations along the closed path. The provision of two such arrays, however, provides higher accuracy of measurements.

ELEMENT LIST
10 optical sensor
12 light source
12a LED
12b LED
12c LED
13 detector assembly
14 light shield
15 array of detectors
16 far detector
17 sensor housing
18 near detector
20 pulse oximeter
21 control unit
22 electronic block
24 microprocessor
26 display

What is claimed is:

1. A method for non-invasive determination of a blood parameter, the method comprising the steps of:

(i) illuminating a measurement location with at least three different wavelenths, a first wavelength $\lambda 1$ lying in a red (R) spectrum, and at least second and third wavelengths $\lambda 2$ and $\lambda 3$ lying substantially in the infrared (IR) spectrum;

(ii) detecting light returned from the measurement location at different detection locations and generating data indicative of the detected light for the different detection locations, wherein said different detection locations are arranged so as to define at least one closed path around the measurement location; and (iii) analyzing the generated data and determining the blood parameter.

2. The method according to claim 1, wherein the analysis of the generated data comprises the steps of:

calculating data indicative of an AC/DC ratio in the light detected at each of the detection locations for the at least three wavelengths;

analyzing the calculated data and determining accepted detection locations to select corresponding AC/DC ratios for each of the at least three wavelengths, $\lambda 1$, $\lambda 2$ and $\lambda 3$; and utilizing the selected ratios for determining the blood parameter.

3. The method according to claim 2, wherein the determination of the blood parameter comprises the steps of:

calculating values of the ratio $W_2/W_3$ for the accepted detection locations in at least one closed path;

analyzing each of the calculated values to determine whether it satisfies a first predetermined condition, so as to generate a signal indicative of that a sensor position is to be adjusted, if the condition is not satisfied;

if the condition is satisfied, determining whether the quality of a photoplethysmogram is acceptable;

if the quality is acceptable, analyzing the selected ratios for calculating ratios $W_1/W_2$ and $W_1/W_3$ from the data detected in at least one closed path, and calculating the differences ABS ($W_1/W_2-W_1/W_3$); and, analyzing the calculated differences for determining whether each of the differences satisfies a second predetermined condition for determining the blood parameter if the condition is satisfied.

4. The method according to claim 3, wherein said first predetermined condition consists of that the calculated value of W2/W3 is inside a predetermined range around the value one, said predeteonined range being defined by the first threshold value, and the second predetermined condition consists of that the calculated difference ABS (W1/W2−W1/W3) is less than certain, second threshold value.

5. A method for non-invasive determination of a blood parameter, the method comprising the steps of:

illuminating a measurement location with at least three different wavelengths, a first wavelength $\lambda 1$ lying in a red (R) spectrum, and at least second and third wavelengths $\lambda 2$ and $\lambda 3$ lying substantially in the infrared (IR) spectrum;

detecting light returned from the measurement location at different detection locations and generating data indicative of the detected light for the different detection locations, wherein said different detection locations are arranged so as to define at least one closed path around the measurement location;

calculating data indicative of an AC/DC ratio in the light detected at each of the detection locations for the at least three wavelengths; and, analyzing the calculated data and determining the blood parameter.

* * * * *